United States Patent
Skålén

(10) Patent No.: US 6,463,816 B1
(45) Date of Patent: Oct. 15, 2002

(54) DEVICE FOR COLLECTING FILTRATE SAMPLES FROM A PULP SUSPENSION

(75) Inventor: Bengt Skålén, Säffle (SE)

(73) Assignee: BTG Källe Inventing AB (SE)

( * ) Notice: Subject to any disclaimer, the term of this patent is extended or adjusted under 35 U.S.C. 154(b) by 0 days.

(21) Appl. No.: 09/508,032

(22) PCT Filed: May 25, 1999

(86) PCT No.: PCT/SE99/00886

§ 371 (c)(1),
(2), (4) Date: Mar. 6, 2000

(87) PCT Pub. No.: WO00/05562

PCT Pub. Date: Feb. 3, 2000

(30) Foreign Application Priority Data

Jul. 10, 1998 (SE) ................................. 9802526

(51) Int. Cl.⁷ .................................................. G01N 1/00
(52) U.S. Cl. .................................................. 73/863.24
(58) Field of Search .................. 73/863.23, 863.24, 73/863.81, 863.83; 162/49; 210/391, 497.1, 396

(56) References Cited

U.S. PATENT DOCUMENTS 4,192,708 A * 3/1980 Bergstrom et al. ............ 162/49
5,011,023 A * 4/1991 Arai ........................ 210/497.1
5,625,157 A   4/1997 Piirainen et al.
6,123,841 A * 9/2000 Gotoh ........................ 210/391

FOREIGN PATENT DOCUMENTS

EP       0724145       7/1996

* cited by examiner

Primary Examiner—Robert Raevis
(74) Attorney, Agent, or Firm—Ostrolenk, Faber, Gerb & Soffen, LLP

(57) ABSTRACT

The invention relates to a device for collecting filtrate samples from a pulp suspension. It comprises a piston rod (3) which, when actuated by a cylinder (2), can reciprocate inside a jacket (5) and which is provided with a filter (4) arranged in an extended position to catch a sample. The filter (4) consists of a wire (6) having a triangular cross-section, the turns (8) of the wire being located close to each other and having their base surface (9) directed outwards and their converging surfaces directed inwards towards the center of the filter (4). During its retracting movement into the jacket the filter (4) is cleaned in the way that fibres which have got stuck on the filter are scraped away by the jacket.

4 Claims, 3 Drawing Sheets

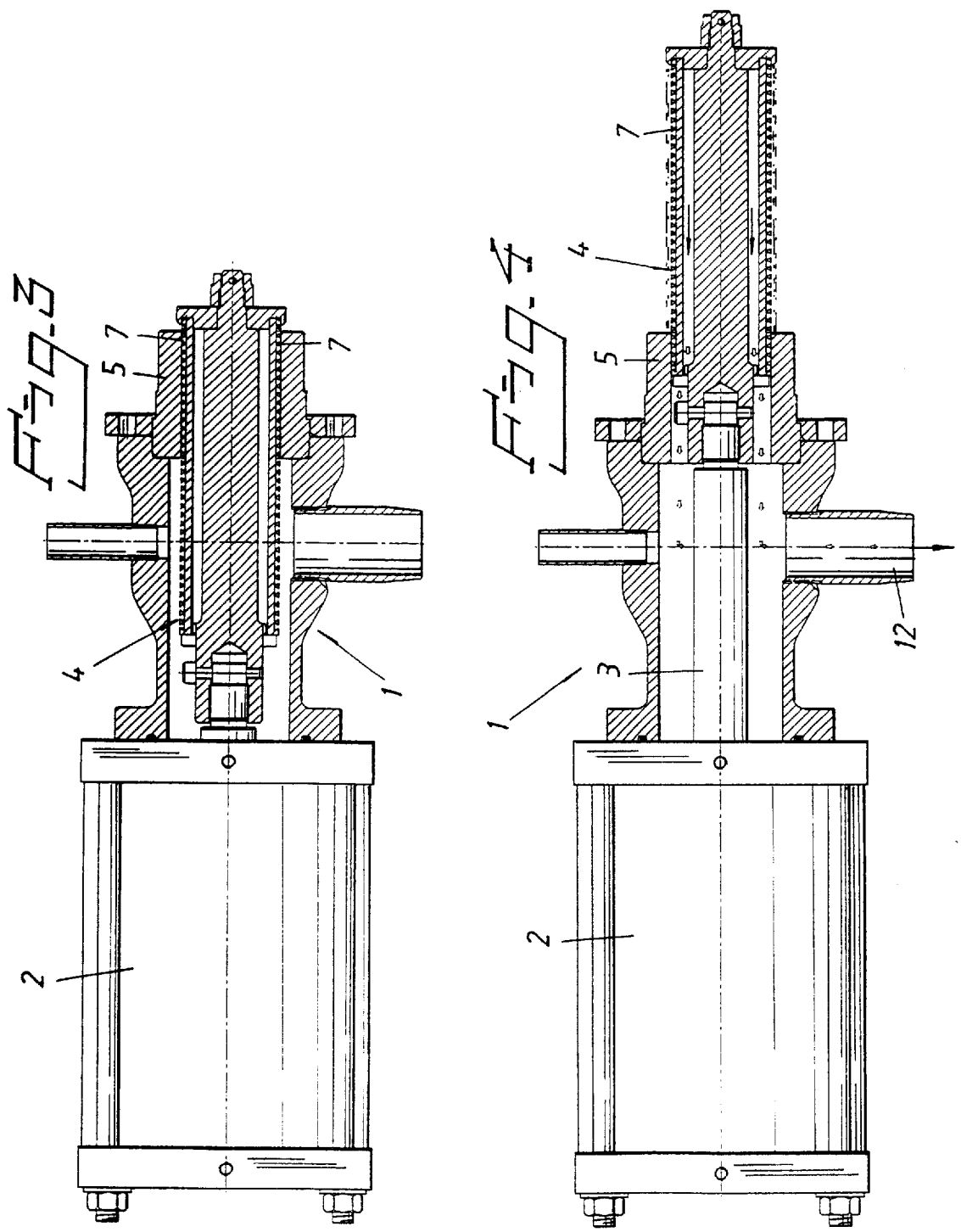

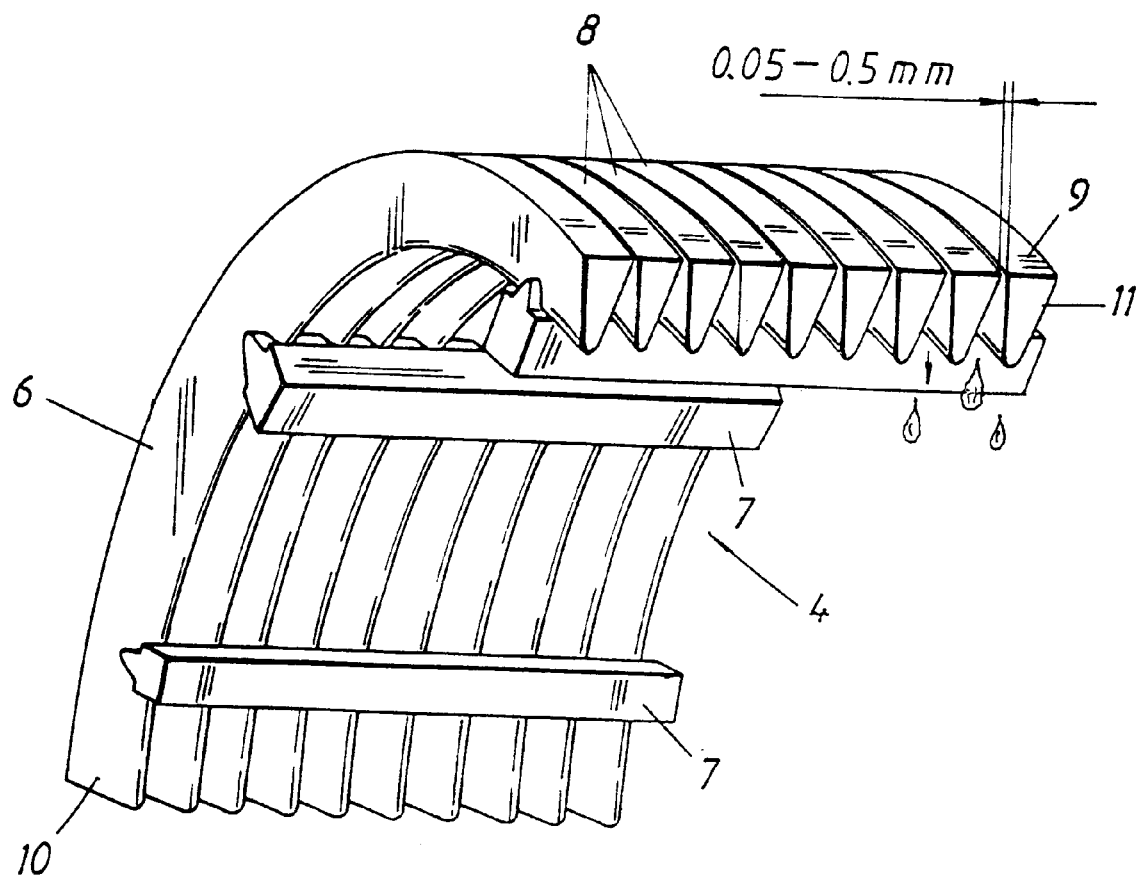

DEVICE FOR COLLECTING FILTRATE SAMPLES FROM A PULP SUSPENSION

The present invention relates to a device for collecting filtrate samples from a pulp suspension, comprising a piston rod arranged, when actuated by a cylinder, to carry out a reciprocating movement in a jacket and supporting a filter which is adapted, when in an extended position, to catch a sample.

In the paper and cellulose industry samples are generally collected from a pulp suspension for the purpose of supervising and controlling the process proper. The samples are analysed for determination of parameters relating to the fibres or to the liquid, i.e. the filtrate, with the intention to determine pH-value, $H_2O_2$-value etcetera. However, the devices used tend to-get clogged by fibres in the pulp suspension. Especially in devices used for on line-measurement in processes it is important that the cleaning and washing of the sampling equipment satisfy the requirements stipulated. The problem in this connection is that those prior art devices require a regular back-flush with air or water to prevent clogging.

The object of the present invention is to eliminate the above-mentioned drawbacks and to provide a filtrate sampler designed so as to automatically clean itself during the sampling process proper with the aid of a reciprocating movement in a jacket.

The features characterizing the invention are set out in the attached claims.

Thanks to the invention there has now been provided a device for collecting filtrate samples of the type mentioned above which in an excellent manner fulfills its purposes and at the same time is both simple and cheap to manufacture. Preferably the sampling device comprises a pneumatic cylinder the piston rod of which is provided with a filter carrying out a reciprocating movement in a jacket when actuated by the cylinder. The filter does basically consist of a number of wires mounted close to each other and having such a configuration that fibres will automatically be scraped away when the pneumatic cylinder retracts the piston rod carrying the filter into said jacket. There is in this way no need to clean the filter with air or water, instead the cleaning takes place when the filter is retracted from an extended position to an inner position in the jacket. When this has taken place the filter returns again out into the pulp suspension in order to catch another sample. The frequency of the operation is determined by inter alia the type of pulp concerned.

One embodiment of the invention is described below, reference being made to the annexed drawing.

FIG. 3 is a cross-sectional view through the filtrate sampler in FIGS. 1 and 2, shown in the retracted position.

FIG. 4 is a cross-sectional view through the filtrate sampler in the extended position.

Figure 1:
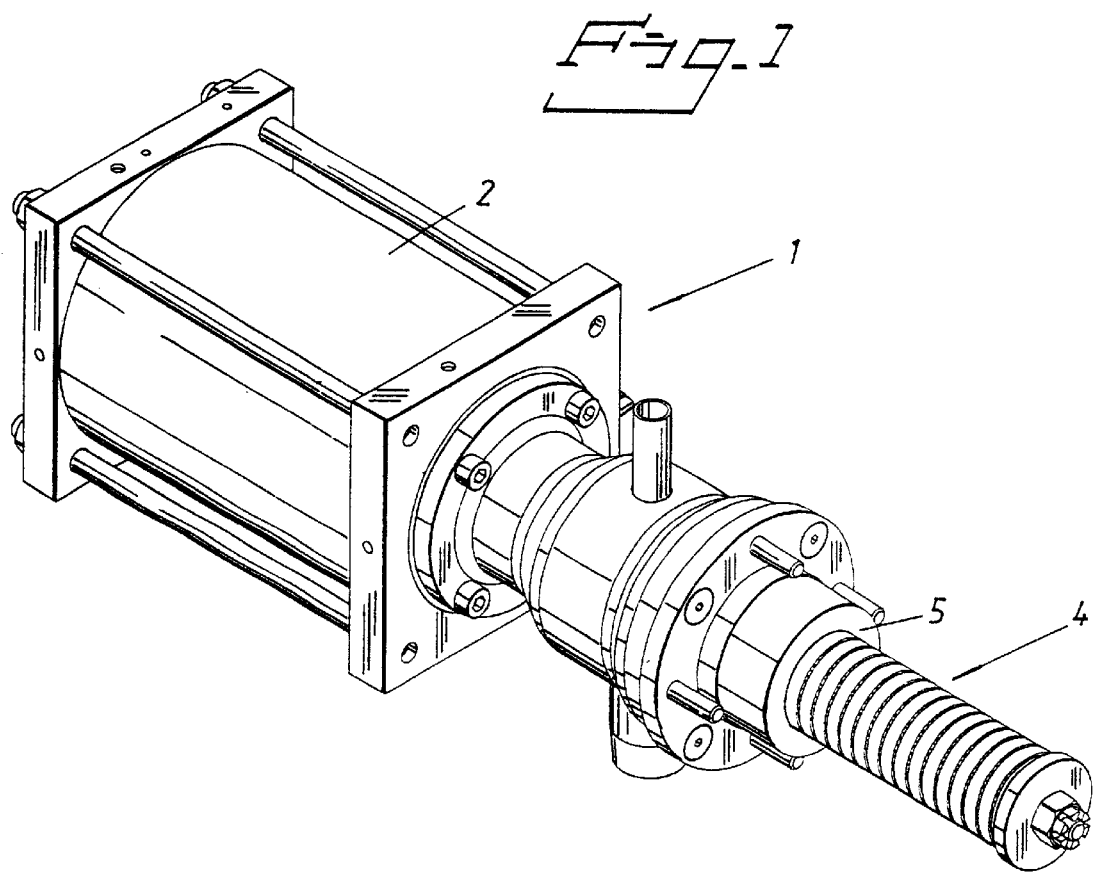
FIGS. 1 and 2 show a filtrate sampler according to the invention, shown in an extended position for sampling and in an inner position, in which fibres which are stuck on the filter are scraped away by the jacket, respectively.
Figure 2:
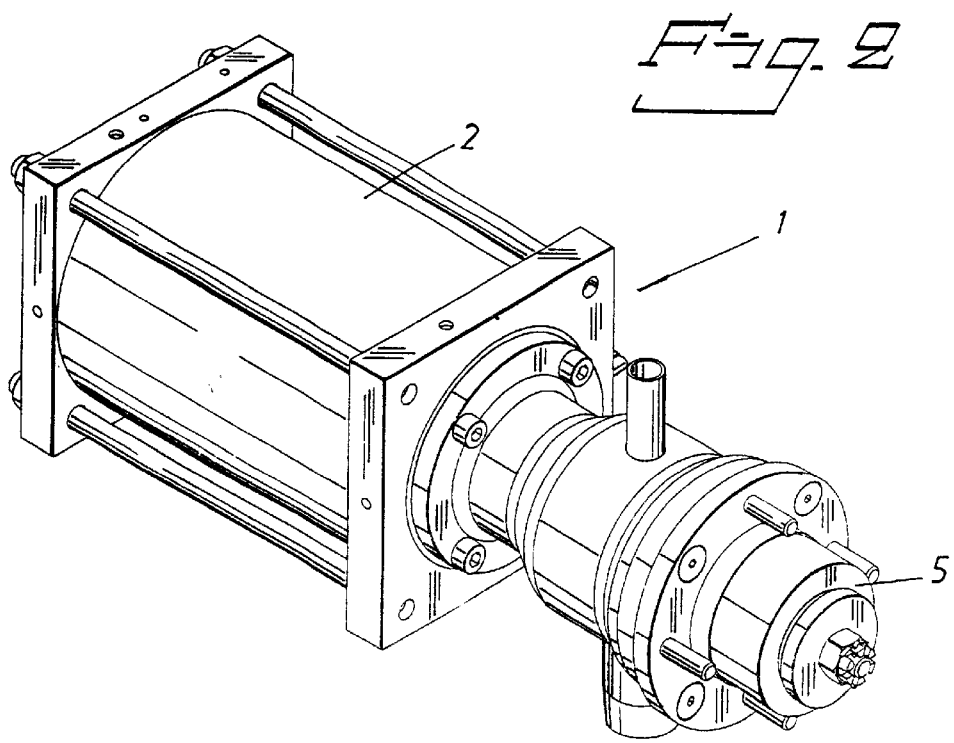

FIG. 5 does, on a greater scale and in a diagrammatic perspective view, show a portion of the filter illustrating its structural design.

As appears from the drawing, the filtrate sampler 1 according to the invention is designed to collect a filtrate sample from a pulp suspension. The sampler 1 comprises a pneumatic cylinder 2 the piston rod 3 of which is provided with a filter 4 attached thereto and arranged to carry out a reciprocating movement inside the jacket 5 when actuated by the pneumatic cylinder. The filter can be made from a wire 6 having a triangular cross-section and comprising wire turns 8 wound like a helical spring. Each individual turn is secured to a number of longitudinal support rods 7. Each of the wire turns 8 has its base surface 9 directed outwards and its converging surfaces 10, 11 directed inwards towards the centre of the filter 4. The distance between the wire turns 8 is determined by the type of pulp studied and can be varied from 0.05 mm up to 0.5 mm. Thanks to the small distance between the wires 8 the fibres cannot penetrate very deeply between them which simplifies the cleaning.

The cleaning of the filtrate sampler 1 according to the invention is carried out without air or water in the way that the filter 4 is moved from its extended position to its inner position. Fibres which have got stuck on the filter 4 can then conveniently be scraped away by the jacket 5. Next the filter 4 is again extended to collect another sample. The cleaning frequency depends on the type of pulp and its concentration.

During the sampling procedure the filtrate oozes out between the triangular wires 8 in the shape of droplets then continuing to an outlet 12 on the jacket 5 and from there to a suitable analyser. Thanks to the triangular cross-section of wires 8 fibres which have penetrated between them will easily accompany the filtrate out from the filter. However, this small amount of fibres has no negative influence.

What is claimed is:

1. A device for collecting filtrate samples from a pulp suspension, comprising a piston rod (3) arranged, when actuated by a cylinder (2), to carry out a reciprocating movement in a jacket (5), and supporting a filter (4) which is adapted, when in an extended position, to collect a sample, characterized i n that the filter (4) is formed by a wire (6) having a substantially triangular cross-section and comprising wire elements (8) disposed close to each other and having their base surface (9) facing outwards and their converging surfaces (10, 11) directed towards the center of the filter (4) which, during its retracting movement into the jacket (5), is cleaned in the way that fibres stuck to the filter are scraped away by the jacket.

2. A device as claimed in claim 1, characterized in that the wire (6) is constituted by wire turns (8) wound like a helical spring, each turn being secured to a number of longitudinal support rods (7).

3. A device as claimed in claim 2, characterized in that the distance between the wire turns (8) can be varied from 0.05 mm to 0.5 mm.

4. A device as claimed in claim 1, characterized in that the distance between the wire turns (8) can be varied from 0.05 mm to 0.5 mm.

* * * * *